US012576249B1

(12) United States Patent
Lorenzo et al.

(10) Patent No.: US 12,576,249 B1
(45) Date of Patent: Mar. 17, 2026

(54) INFUSION CATHETER AND BALLOON CATHETER SYSTEM AND METHOD

(71) Applicant: Caliber Therapeutics, LLC, New Hope, PA (US)

(72) Inventors: Juan A. Lorenzo, New Hope, PA (US); Tyson A. Montidoro, New Hope, PA (US); Darren R. Sherman, New Hope, PA (US); Drew A. Jones, New Hope, PA (US); Michael A. Lorenzo, New Hope, PA (US)

(73) Assignee: Caliber Therapeutics, LLC, New Hope, PA (US)

( * ) Notice: Subject to any disclaimer, the term of this patent is extended or adjusted under 35 U.S.C. 154(b) by 0 days.

(21) Appl. No.: 19/217,972

(22) Filed: May 23, 2025

(51) Int. Cl.
   *A61M 25/10* (2013.01)
   *A61M 25/00* (2006.01)
(52) U.S. Cl.
   CPC ........ *A61M 25/10* (2013.01); *A61M 25/0043* (2013.01); *A61M 2025/0057* (2013.01); *A61M 2202/0007* (2013.01); *A61M 2210/12* (2013.01)
(58) Field of Classification Search
   CPC .............. A61M 25/10; A61M 25/0043; A61M 2025/0057
   See application file for complete search history.

(56) References Cited

U.S. PATENT DOCUMENTS

| | | | |
|---|---|---|---|
| 5,320,604 A * | 6/1994 | Walker ................. | A61M 25/10 604/99.04 |
| 5,356,388 A * | 10/1994 | Sepetka ............ | A61M 25/0069 604/524 |
| 11,071,847 B1 | 7/2021 | Orth et al. | |
| 2007/0093782 A1 | 4/2007 | Kugler et al. | |
| 2012/0259216 A1 * | 10/2012 | Gerrans ......... | A61B 17/320725 604/514 |
| 2022/0265292 A1 | 8/2022 | Carpenter et al. | |

* cited by examiner

*Primary Examiner* — Erin McGrath
(74) *Attorney, Agent, or Firm* — Crockett & Crockett, PC; K. David Crockett, Esq.

(57) ABSTRACT

Systems and methods for treatment of vascular lesions. The system includes a drug-eluting distal portion of a drug-eluting catheter and a balloon of a balloon catheter configured for positioning with a vascular lesion. The method entails securing the drug-eluting distal portion to the inner wall of a blood vessel with the balloon, and delivery of therapeutic agents into the blood vessel wall while the drug-eluting distal portion is held against the wall of the blood vessel by the balloon. The distal infusion portion of the drug infusion catheter is first located within the lesion. After the drug infusion portion is in position, the balloon of the balloon catheter is translated into the lesion and inflated to press the drug-eluting portion into contact with the blood vessel wall and a therapeutic agent is delivered through the drug-eluting portion.

4 Claims, 2 Drawing Sheets

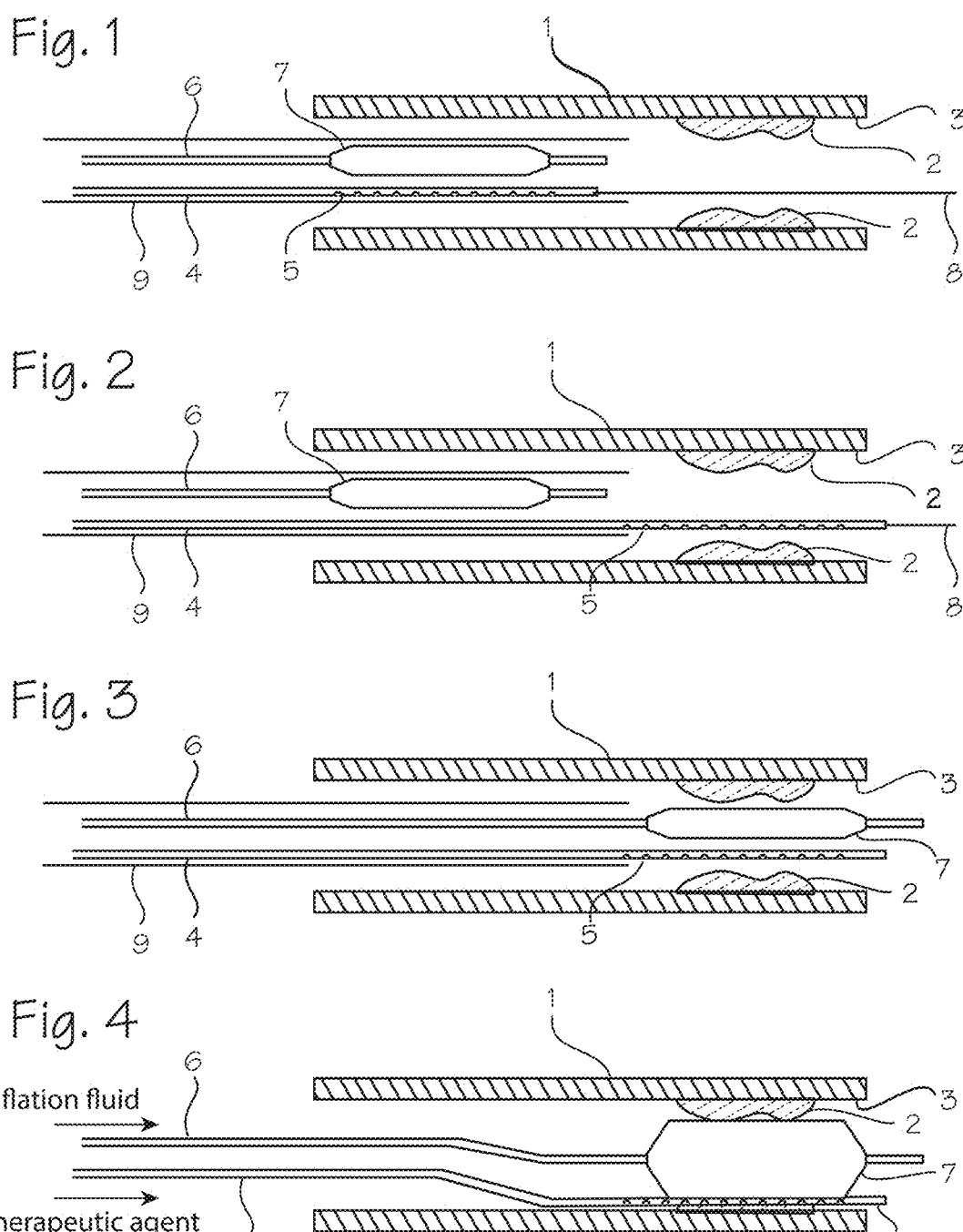

INFUSION CATHETER AND BALLOON CATHETER SYSTEM AND METHOD

FIELD OF THE INVENTIONS

The inventions described below relate to the field of treatment of vascular disease, and more specifically to the field of drug delivery to luminal walls of blood vessels.

BACKGROUND OF THE INVENTIONS

Local drug delivery of drugs to the wall of blood vessels is used to treat stenosis and restenosis, thrombus, atherosclerosis and other vascular diseases. Various references disclose catheter systems for local delivery of therapeutic agents to the inner walls of blood vessels to treat these conditions. These devices include catheters with drug-eluting balloons and drug delivery catheters, and catheter systems with combined drug delivery catheters joined to angioplasty balloons. For example, Kruger et al., Endovascular Devices and Methods, U.S. Pub. 2007/0093782 (Apr. 26, 2007) and Carpenter, et al., Method and Apparatus for Delivery of Cell Therapies, U.S. Pub. 2022/0265292 (Aug. 25, 2002) disclose drug delivery catheters with drug-eluting distal portions fixed to the outside of balloons. In use, the balloon and the drug-eluting distal portions which are fixed to the balloon are pushed into a vascular lesion, fixed to each other, to place both components within a lesion. With the drug-eluting distal portions and fixed balloon disposed with the blood vessel and spanning the lesion, the balloon is inflated to press the drug-eluting distal portions into close contact with the blood vessel wall, and therapeutic agents are delivered to the blood vessel wall through the drug-eluting distal portions of the catheter.

SUMMARY

The catheter systems and methods described below provide for treatment of vascular lesions with a drug-eluting distal portion of a drug-eluting catheter and a balloon of a balloon catheter disposed within or along a lesion of a blood vessel. The method entails securing the drug-eluting distal portion of the drug-eluting catheter to the inner wall of a blood vessel with the balloon of the balloon catheter, and delivery of therapeutic agents into the blood vessel wall while the drug-eluting distal portion is held against the wall of the blood vessel by the balloon. The system comprises a balloon catheter and a drug infusion catheter that are separately translatable within the vasculature. The distal infusion portion of the drug infusion catheter is first located within the lesion. After the drug infusion portion is in position, the balloon of the balloon catheter is translated into the lesion and inflated to press the drug-eluting portion into contact with the blood vessel wall. With the balloon inflated and the drug-eluting portion pressed against the blood vessel wall, a therapeutic agent is delivered through the drug-eluting portion and into the blood vessel wall.

BRIEF DESCRIPTION OF THE DRAWINGS

FIG. 1 illustrates the distal portions of the balloon catheter and drug-eluting catheter within a blood vessel.

FIG. 2 illustrates a step of advancing the drug-eluting portion of the drug-eluting catheter into position proximate a lesion in the blood vessel.

FIG. 3 illustrates a subsequent step of advancing the balloon of the balloon catheter into position proximate the lesion in the blood vessel and the previously placed drug-eluting portion.

FIG. 4 illustrates the steps of inflating the balloon and delivering a therapeutic agent through the drug-eluting position and into the blood vessel wall.

DETAILED DESCRIPTION OF THE INVENTIONS

Figures 5, 6:
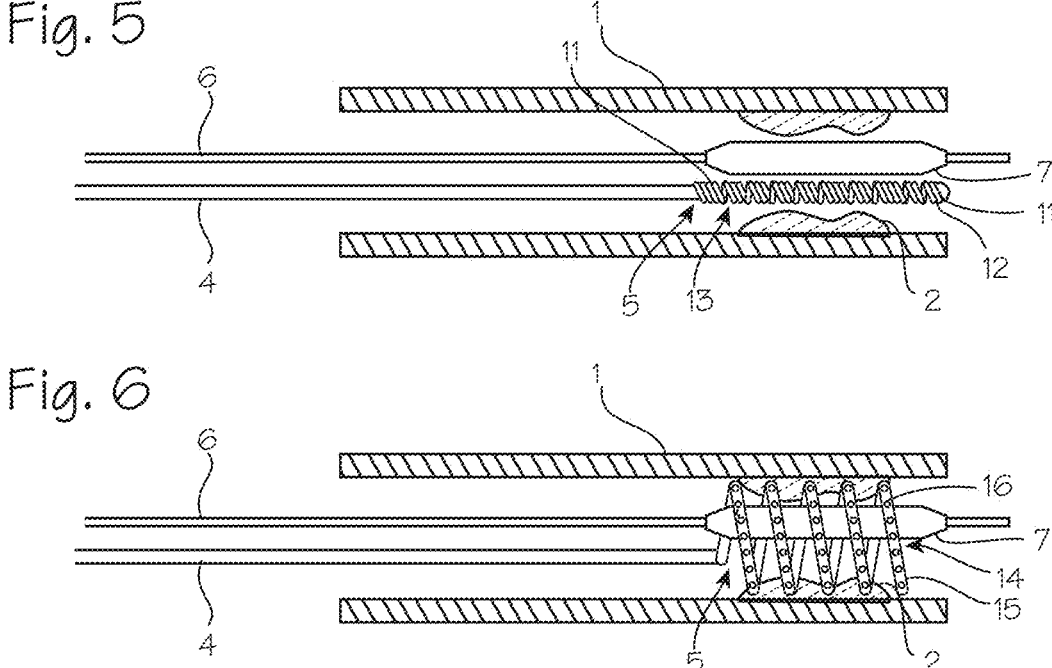
FIG. 5 illustrates a version of the system in which the drug-eluting portion comprises a coiled-wire tube.
FIG. 6 illustrates a version of the system in which the drug-eluting portion comprises a helically coiled tube.

FIG. 1 illustrates a blood vessel 1 of a patient, and a lesion 2 within the blood vessel, proximate the blood vessel wall 3. The blood vessel is occluded by the lesion. A drug-eluting catheter 4 has been navigated through the patient's vasculature, to position the drug-eluting portion 5 proximal to the lesion. A balloon catheter 6 has been navigated through the patient's vasculature to position the balloon 7 proximal to the lesion. To this point, the drug-eluting catheter and balloon catheter may be delivered in tandem (one following the other) or together. The method preferably includes navigating the drug-eluting catheter and the balloon catheter in tandem, through a guide catheter 9, to position the drug-eluting portion 5 proximal to the lesion and to position the balloon proximal to the lesion, wherein the drug-eluting catheter and the balloon catheter are disposed side-by-side within the guide catheter and are separately translatable within the vasculature. (Here, "proximal" to the approach to the lesion, whether approached from a proximal or distal region of the blood vessel itself, and "distal" to the lesion refers to the extent of the blood vessel opposite the approaching catheter. This may or may not correspond to the terms proximal or distal in reference to the blood vessel itself.)

FIG. 2 illustrates a step of advancing the drug-eluting portion of the drug-eluting catheter into position proximate a lesion in the blood vessel. The drug-eluting catheter is translatable relative to the balloon catheter, so that the drug-eluting portion may be advanced into the lesion while the balloon catheter remains in place proximal to the lesion. Advancement of the drug-eluting catheter may be aided with a guidewire 8, in which case a guide wire is advanced through the lesion, and thereafter the drug-eluting catheter is advanced over the guidewire, and the guidewire is then withdrawn.

FIG. 3 illustrates a subsequent step of advancing the balloon of the balloon catheter into position proximate the lesion in the blood vessel and the previously placed drug-eluting portion.

FIG. 4 illustrates the steps of inflating the balloon and delivering a therapeutic agent through the drug-eluting position and into the blood vessel wall. In these steps, the balloon is inflated to press the drug-eluting portion into the lesion, or the wall of the blood vessel (the luminal surface and/or inner layers of the blood vessel). With the drug-eluting portion pressed against the lesion of the blood vessel wall (which may entail contact with the surface (luminal wall) of the blood vessel itself, the surface of the lesion, or intrusion into the bulk of the lesion. Therapeutic agents may then be delivered through the drug delivery catheter and into the lesion or layers of the blood vessel.

The drug-eluting portion is depicted in the figures as a straight distal portion. The drug-eluting portion may also be helical and made of a resilient or superelastic material capable of being resiliently straightened and assuming a small delivery configuration for insertion into a guide catheter for delivery through the vasculature, and capable of resiliently or superelastically reverting toward a predetermined and/or trained helical configuration. In the case of a helical drug-eluting portion, the balloon may be translated into the center of the helix, and expanded to press the helix into contact with all of the circumference of the blood vessel wall or lesion.

After delivery of therapeutic agents, the balloon may be deflated, and the catheters may be withdrawn from the lesion and the patient's body.

FIG. 5 illustrates a version of the system in which the drug-eluting portion 5 comprises a coiled-wire tube. The coiled-wire tube 11 is disposed at the distal end of the drug-eluting catheter 4, and comprises a number of helical coil turns 12 with several gaps 13 between the coil turns through which a therapeutic agent may be injected into the lesion or blood vessel wall. As with the previously mentioned drug-eluting portions, the coiled-wire tube may be pressed into contact with the lesion or blood vessel wall by the balloon (disposed beside the coiled-wire tube 11), so that therapeutic agents forced from the drug-eluting portion are delivered to the blood vessel in close proximity to the blood vessel wall or lesion.

FIG. 6 illustrates a version of the system in which the drug-eluting portion comprises a tube wound into a helix, i.e. a helically coiled tube 14. The helically coiled tube 14 is disposed at the distal end of the drug-eluting catheter 4, and comprises a number of helical coil turns 15, with numerous apertures 16 in outwardly facing surfaces of the helically coiled tube 14. The helically coiled tube 14 has a lumen passing through the helix, which accommodates the balloon. The helical drug-eluting portion is resiliently (elastically or pseudoelastically) deformable, with the helically coiled unconstrained configuration toward which it returns when released from the constraint of a guide catheter and a constrained configuration conforming to the lumen of a delivery catheter through which it is delivered.

The system and method may be used to treat and/or inhibit stenosis/restenosis, in which case suitable therapeutic agents may include paclitaxel and rapamycin. The system and method may be used to treat and/or inhibit thrombosis, in which case suitable therapeutic agents may include antiplatelet agents and anticoagulants. The system and method may be used to treat and/or inhibit atherosclerosis, in which case suitable therapeutic agents may include interleukins, protein kinase inhibitors, p38 mitogen-activated protein kinase (MAPK) inhibitor, P-Selectin, or colchicine.

In use, the systems are used in a method to treat a lesion 2 in a blood vessel 1 in a patient's vasculature, where a surgeon may deliver a therapeutic agent to a lesion or the wall of a blood vessel. In this method, the surgeon will:

navigate a drug-eluting catheter 4 with a drug-eluting distal portion 5 through the patient's vasculature, to position the drug-eluting portion 5 proximal to the lesion;

navigate a balloon catheter 6 with balloon 7 disposed on the distal end of the balloon catheter through the patient's vasculature, to position the balloon proximal to the lesion;

further navigate the drug-eluting portion distally into the lesion, leaving the balloon in position proximal to the lesion;

thereafter further navigate the balloon distally into the lesion, such that the balloon is longitudinally aligned, within the lesion, with the drug-eluting portion;

inflate the balloon to press the drug-eluting portion into contact with the lesion or the wall of the blood vessel;

with the balloon inflated and the drug-eluting portion pressed into contact with the lesion or the wall of the blood vessel, deliver a therapeutic agent through the drug-eluting portion to the lesion or the wall of the blood vessel; and withdraw the drug-eluting catheter and balloon catheter from the blood vessel.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A method of treating a lesion (2) in a blood vessel (1) in a patient's vasculature, said method comprising the steps of:

navigating a drug-eluting catheter (4) with a drug-eluting distal portion (5) through the patient's vasculature, to position the drug-eluting portion (5) proximal to the lesion;

navigating a balloon catheter (6) with a balloon (7) disposed on a distal end of the balloon catheter through the patient's vasculature, to position the balloon proximal to the lesion; wherein wherein the steps of navigating the drug-eluting catheter and navigating the balloon catheter include navigating the drug-eluting catheter and navigating the balloon catheter in tandem, through a guide catheter, to position the drug-eluting portion (5) proximal to the lesion and to position the balloon proximal to the lesion, wherein the drug-eluting catheter and the balloon catheter are disposed side-by-side within the guide catheter and are separately translatable within the vasculature; and further navigating the drug-eluting portion distally into the lesion, leaving the balloon in position proximal to the lesion;

thereafter further navigating the balloon distally into the lesion, such that the balloon is longitudinally aligned, within the lesion, with the drug-eluting portion;

inflating the balloon to press the drug-eluting portion into contact with the lesion or a wall of the blood vessel;

with the balloon inflated and the drug-eluting portion pressed into contact with the lesion or the wall of the blood vessel, delivering a therapeutic agent through the drug-eluting portion to the lesion or the wall of the blood vessel; and withdrawing the drug-eluting catheter and balloon catheter from the blood vessel.

2. A method of treating a lesion (2) in a blood vessel (1) in a patient's vasculature, said method comprising the steps of:

navigating a drug-eluting catheter (4) with a drug-eluting distal portion (5) through the patient's vasculature, to position the drug-eluting portion (5) proximal to the lesion; wherein the drug-eluting portion comprises a section of a tube with a plurality of apertures, said section being resiliently biased to revert toward a straight configuration when unconstrained;

navigating a balloon catheter (6) with a balloon (7) disposed on a distal end of the balloon catheter through the patient's vasculature, to position the balloon proximal to the lesion; wherein further navigating the drug-eluting portion distally into the lesion, leaving the balloon in position proximal to the lesion;

thereafter further navigating the balloon distally into the lesion, such that the balloon is longitudinally aligned, within the lesion, with the drug-eluting portion;

inflating the balloon to press the drug-eluting portion into contact with the lesion or a wall of the blood vessel;

with the balloon inflated and the drug-eluting portion pressed into contact with the lesion or the wall of the blood vessel, delivering a therapeutic agent through the drug-eluting portion to the lesion or the wall of the blood vessel; and withdrawing the drug-eluting catheter and balloon catheter from the blood vessel.

3. A method of treating a lesion (2) in a blood vessel (1) in a patient's vasculature, said method comprising the steps of:

navigating a drug-eluting catheter (4) with a drug-eluting distal portion (5) through the patient's vasculature, to position the drug-eluting portion (5) proximal to the lesion; wherein the drug-eluting portion comprises a helically coiled wire with a plurality of coil turns with gaps between turns of the coil, and the step of delivering a therapeutic agent through the drug-eluting portion comprises delivering therapeutic agent through the gaps in the coil;

navigating a balloon catheter (6) with a balloon (7) disposed on a distal end of the balloon catheter through the patient's vasculature, to position the balloon proximal to the lesion; wherein further navigating the drug-eluting portion distally into the lesion, leaving the balloon in position proximal to the lesion;

thereafter further navigating the balloon distally into the lesion, such that the balloon is longitudinally aligned, within the lesion, with the drug-eluting portion;

inflating the balloon to press the drug-eluting portion into contact with the lesion or a wall of the blood vessel;

with the balloon inflated and the drug-eluting portion pressed into contact with the lesion or the wall of the blood vessel, delivering a therapeutic agent through the drug-eluting portion to the lesion or the wall of the blood vessel; and withdrawing the drug-eluting catheter and balloon catheter from the blood vessel.

4. A method of treating a lesion (2) in a blood vessel (1) in a patient's vasculature, said method comprising the steps of:

navigating a drug-eluting catheter (4) with a drug-eluting distal portion (5) through the patient's vasculature, to position the drug-eluting portion (5) proximal to the lesion; wherein the drug-eluting portion comprises a section of a helically coiled tube with a plurality of apertures, said section being resiliently biased to revert toward a helically coiled configuration when unconstrained;

navigating a balloon catheter (6) with a balloon (7) disposed on a distal end of the balloon catheter through the patient's vasculature, to position the balloon proximal to the lesion; wherein further navigating the drug-eluting portion distally into the lesion, leaving the balloon in position proximal to the lesion;

thereafter further navigating the balloon distally into the lesion, such that the balloon is longitudinally aligned, within the lesion, with the drug-eluting portion;

inflating the balloon to press the drug-eluting portion into contact with the lesion or a wall of the blood vessel;

with the balloon inflated and the drug-eluting portion pressed into contact with the lesion or the wall of the blood vessel, delivering a therapeutic agent through the drug-eluting portion to the lesion or the wall of the blood vessel; and withdrawing the drug-eluting catheter and balloon catheter from the blood vessel.

\* \* \* \* \*